United States Patent [19]

Koerwer

[11] Patent Number: 5,624,822
[45] Date of Patent: Apr. 29, 1997

[54] HIRUDIN FUSION PROTEINS AND PREPARATION OF HIRUDIN

[75] Inventor: Wolfgang Koerwer, Gruenstadt, Germany

[73] Assignee: BASF Aktiengesellschaft, Ludwigshafen, Germany

[21] Appl. No.: 262,384

[22] Filed: Jun. 20, 1994

Related U.S. Application Data

[63] Continuation of Ser. No. 861,820, filed as PCT/EP90/02084, Dec. 4, 1990 published as WO91/09946, Jul. 11, 1991, abandoned.

[30] Foreign Application Priority Data

Dec. 22, 1989 [DE] Germany ............... 39 42 580.0

[51] Int. Cl.$^6$ ............... C12P 21/06; C12N 5/00; C07K 14/815
[52] U.S. Cl. ............... 435/69.7; 435/69.1; 435/320.1; 530/300; 530/350
[58] Field of Search ............... 435/69.1, 69.7, 435/370.1, 240.1; 530/350, 855, 300; 935/10, 97, 98, 6

[56] References Cited

U.S. PATENT DOCUMENTS

| | | | |
|---|---|---|---|
| 5,118,790 | 6/1992 | Winant et al. | 530/324 |
| 5,164,304 | 11/1992 | Johnson et al. | 435/69.1 |
| 5,166,318 | 11/1992 | Furutani et al. | 530/381 |

FOREIGN PATENT DOCUMENTS

| | | |
|---|---|---|
| 0135532 | 4/1985 | European Pat. Off. . |
| 8403103 | 8/1984 | WIPO . |

OTHER PUBLICATIONS

Merck Index, (1983) 10th Ed. #4613.
Dodt et al. The Complete Amino Acid Sequence of Hirudin, a Thrombin Specific Inhibitor. FEBS Lett. 165 (2) 180 (1984).
Dodt et al. Expression, Secretion and Processing of Hirudin in *E. coli* Using the Alkaline Phosphatase Signal Sequence FEBS Lett. 202 (2) 373 (1986).
Bergmann et al. Chemical Synthesis & Expression of a Gene Coding for Hirudin Biol. Chem. Hoppe–Seyles 367: 731 (1986).
Fortkamp et al. Cloning and Expression in *E. coli* of a Synthetic DNA for Hirudin DNA, 5, 511 (1986).
Dersenhofer, Crystallographic Refinement and Atomic Models of a Human F$_c$ Fragment Biochemistry 20, 2361–96 (1981).
Mokg et al. Eur J. Biochem. 156:637 (1986).
Uhlen et al. 1984 J Biol Chem 259(3): 1695–1702.
Moks et al. Biochemistry vol. 26 pp. 5239–5244 (1987).

*Primary Examiner*—Robert A. Wax
*Assistant Examiner*—K. Cochrane Carlson
*Attorney, Agent, or Firm*—Keil & Weinkauf

[57] ABSTRACT

Fusion proteins composed of protein A and hirudin peptides are used to prepare hirudin peptides.

4 Claims, 2 Drawing Sheets

SEQUENCE LISTING ( 1 ) GENERAL INFORMATION:

( i i i ) NUMBER OF SEQUENCES: 10

( 2 ) INFORMATION FOR SEQ ID NO: 1:

( i ) SEQUENCE CHARACTERISTICS:
        ( A ) LENGTH: 97 base pairs
        ( B ) TYPE: nucleic acid
        ( C ) STRANDEDNESS: double
        ( D ) TOPOLOGY: linear ( x i ) SEQUENCE DESCRIPTION: SEQ ID NO: 1:

```
AGCT TCT AAC AAT TTC AAC AAA GAA CAA CAA AAT GCT TTC TAT GAA ATC      49
     Ser Asn Asn Phe Asn Lys Glu Gln Gln Asn Ala Phe Tyr Glu Ile
     1               5                   10                  15

TTG CAT TTA CCT AAC TTA AAC GAA GAA CAA CGC AAT GGT TTC ATC CAG       97
Leu His Leu Pro Asn Leu Asn Glu Glu Gln Arg Asn Gly Phe Ile Gln
                20                  25                  30
```

( 2 ) INFORMATION FOR SEQ ID NO: 2:

( i ) SEQUENCE CHARACTERISTICS:
        ( A ) LENGTH: 97 base pairs
        ( B ) TYPE: nucleic acid
        ( C ) STRANDEDNESS: double
        ( D ) TOPOLOGY: linear ( x i ) SEQUENCE DESCRIPTION: SEQ ID NO: 2:

```
AGCT CTG GAT GAA ACC ATT GCG TTG TTC TTC GTT TAA GTT AGG TAA ATG      49
     Gln Ile Phe Gly Asn Arg Gln Glu Glu Asn Leu Asn Pro Leu His
     1               5                   10                  15

CAA GAT TTC ATA GAA AGC ATT TTG TTG TTC TTT GTT GAA ATT GTT AGA       97
Leu Ile Glu Tyr Phe Ala Asn Gln Gln Glu Lys Asn Phe Asn Asn Ser
                20                  25                  30
```

( 2 ) INFORMATION FOR SEQ ID NO: 3:

( i ) SEQUENCE CHARACTERISTICS:
        ( A ) LENGTH: 129 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 3:

```
AATTCAAAAA  CCAAACCGCG  TATCAAAACC  ATGGTTGTTT  ACACTGACTG  CACTGAATCC    60
GGTCAGAACC  TGTGCCTGTG  CGAAGGCTCT  AACGTTTGCG  GCCAGGGCAA  CAAATGCATC   120
CTGGGCTCT                                                                129
```

( 2 ) INFORMATION FOR SEQ ID NO: 4:

( i ) SEQUENCE CHARACTERISTICS:
        ( A ) LENGTH: 106 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 4:

```
GACGGCGAAA  AAAACCAGTG  CGTTACTGGC  GAAGGTACCC  CGAAACCGCA  GTCTCACAAC    60
GACGGCGACT  TCGAAGAAAT  CCCGGAAGAA  TACCTGCAGT  AATAGG                  106
```

( 2 ) INFORMATION FOR SEQ ID NO: 5:

( i ) SEQUENCE CHARACTERISTICS:
        ( A ) LENGTH: 128 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 5:

```
TCGACCTATT  ACTGCAGGTA  TTCTTCCGGG  ATTTCTTCGA  AGTCGCCGTC  GTTGTGAGAC    60
TGCGGTTTCG  GGGTACCTTC  GCCAGTAACG  CACTGGTTTT  TTTCGCCGTC  AGAGCCCAGG   120
ATGCATTT                                                                128
```

( 2 ) INFORMATION FOR SEQ ID NO: 6:

( i ) SEQUENCE CHARACTERISTICS:
        ( A ) LENGTH: 106 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 6:

```
GTTGCCCTGG  CCGCAAACGT  TAGAGCCTTC  GCACAGGCAC  AGGTTCTGAC  CGGATTCAGT    60
GCAGTCAGTG  TAAACAACCA  TGGTTTGATA  CGCGGTTTGG  TTTTG                   106
```

( 2 ) INFORMATION FOR SEQ ID NO: 7:

( i ) SEQUENCE CHARACTERISTICS:
        ( A ) LENGTH: 235 base pairs
        ( B ) TYPE: nucleic acid
        ( C ) STRANDEDNESS: double
        ( D ) TOPOLOGY: linear ( x i ) SEQUENCE DESCRIPTION: SEQ ID NO: 7:

```
AATTCAAAAA  CCAAACCGCG  TATCAAAACC  ATGGTTGTTT  ACACTGACTG  CACTGAATCC    60
GGTCAGAACC  TGTGCCTGTG  CGAAGGCTCT  AACGTTTGCG  GCCAGGGCAA  CAAATGCATC   120
CTGGGCTCTG  ACGGCGAAAA  AAACCAGTGC  GTTACTGGCG  AAGGTACCCC  GAAACCGCAG   180
```

5,624,822

11

12

-continued

TCTCACAACG ACGGCGACTT CGAAGAAATC CCGGAAGAAT ACCTGCAGTA ATAGG        235

( 2 ) INFORMATION FOR SEQ ID NO: 8:

( i ) SEQUENCE CHARACTERISTICS:
        ( A ) LENGTH: 235 base pairs
        ( B ) TYPE: nucleic acid
        ( C ) STRANDEDNESS: double
        ( D ) TOPOLOGY: linear ( x i ) SEQUENCE DESCRIPTION: SEQ ID NO: 8:

TCGACCTATT ACTGCAGGTA TTCTTCCGGG ATTTCTTCGA AGTCGCCGTC GTTGTGAGAC        60

TGCGGTTTCG GGGTACCTTC GCCAGTAACG CACTGGTTTT TTTCGCCGTC AGAGCCCAGG       120

ATGCATTTGT TGCCCTGGCC GCAAACGTTA GAGCCTTCGC ACAGGCACAG GTTCTGACCG       180

GATTCAGTGC AGTCAGTGTA AACAACCATG GTTTTGATAC GCGGTTTGGT TTTTG           235

( 2 ) INFORMATION FOR SEQ ID NO: 9:

( i ) SEQUENCE CHARACTERISTICS:
        ( A ) LENGTH: 726 base pairs
        ( B ) TYPE: nucleic acid
        ( C ) STRANDEDNESS: double
        ( D ) TOPOLOGY: linear ( x i ) SEQUENCE DESCRIPTION: SEQ ID NO: 9:

```
ATG GAA CAA CGC ATA ACC CTG AAA GAA GCT TCT AAC AAT TTC AAC AAA         48
Met Glu Gln Arg Ile Thr Leu Lys Glu Ala Ser Asn Asn Phe Asn Lys
1                 5                  10                  15

GAA CAA CAA AAT GCT TTC TAT GAA ATC TTG CAT TTA CCT AAC TTA AAC         96
Glu Gln Gln Asn Ala Phe Tyr Glu Ile Leu His Leu Pro Asn Leu Asn
            20                  25                  30

GAA GAA CAA CGC AAT GGT TTC ATC CAG AGC TTA AAA GAT GAC CCA AGC        144
Glu Glu Gln Arg Asn Gly Phe Ile Gln Ser Leu Lys Asp Asp Pro Ser
        35                  40                  45

CAA AGT GCT AAC CTA TTG TCA GAA GCT AAA AAG TTA AAT GAA TCT CAA        192
Gln Ser Ala Asn Leu Leu Ser Glu Ala Lys Lys Leu Asn Glu Ser Gln
    50                  55                  60

GCA CCG AAA GCG GAT AAC AAA TTC AAC AAA GAA CAA CAA AAT GCT TTC        240
Ala Pro Lys Ala Asp Asn Lys Phe Asn Lys Glu Gln Gln Asn Ala Phe
65                  70                  75                  80

TAT GAA ATC TAA CAT TTA CCT AAC TTA AAC GAA GAA CAA CGC AAT GGT        288
Tyr Glu Ile Leu His Leu Pro Asn Leu Asn Glu Glu Gln Arg Asn Gly
                85                  90                  95

TTC ATC CAA AGC CTA AAA GAT GAC CCA AGC CAA AGC GCT AAC CTT TTA        336
Phe Ile Gln Ser Leu Lys Asp Asp Pro Ser Gln Ser Ala Asn Leu Leu
            100                 105                 110

GCA GAA GCT AAA AAG CTA AAT GAT GCT CAA GCA CCA AAA GCT GAC AAC        384
Ala Glu Ala Lys Lys Leu Asn Asp Ala Gln Ala Pro Lys Ala Asp Asn
        115                 120                 125

AAA TTC AAC AAA GAA CAA CAA AAT GCT TTC TAT GAA ATT TTA CAT TTA        432
Lys Phe Asn Lys Glu Gln Gln Asn Ala Phe Tyr Glu Ile Leu His Leu
    130                 135                 140

CCT AAC TTA ACT GAA GAA CAA CGT AAC GGC TTC ATC CAA AGC CTT AAA        480
Pro Asn Leu Thr Glu Glu Gln Arg Asn Gly Phe Ile Gln Ser Leu Lys
145                 150                 155                 160

GAC GAT CCG GGG AAT TCA AAA ACC AAA CCG CGT ATC AAA ACC ATG GTT        528
Asp Asp Pro Gly Asn Ser Lys Thr Lys Pro Arg Ile Lys Thr Met Val
                165                 170                 175

GTT TAC ACT GAC TGC ACT GAA TCC GGT CAG AAC CTG TGC CTG TGC GAA        576
Val Tyr Thr Asp Cys Thr Glu Ser Gly Gln Asn Leu Cys Leu Cys Glu
                180                 185                 190
```

```
GGC  TCT  AAC  GTT  TGC  GGC  CAG  GGC  AAC  AAA  TGC  ATC  CTG  GGC  TCT  GAC        624
Gly  Ser  Asn  Val  Cys  Gly  Gln  Gly  Asn  Lys  Cys  Ile  Leu  Gly  Ser  Asp
     195                      200                     205

GGC  GAA  AAA  AAC  CAG  TGC  GTT  ACT  GGC  GAA  GGT  ACC  CCG  AAA  CCG  CAG        672
Gly  Glu  Lys  Asn  Gln  Cys  Val  Thr  Gly  Glu  Gly  Thr  Pro  Lys  Pro  Gln
210                      215                     220

TCT  CAC  AAC  GAC  GGC  GAC  TTC  GAA  GAA  ATC  CCG  GAA  GAA  TAC  CTG  CAG        720
Ser  His  Asn  Asp  Gly  Asp  Phe  Glu  Glu  Ile  Pro  Glu  Glu  Tyr  Leu  Gln
225                      230                     235                     240

TAATAG                                                                                 726
```

(2) INFORMATION FOR SEQ ID NO: 10:

(i) SEQUENCE CHARACTERISTICS:
        (A) LENGTH: 726 base pairs
        (B) TYPE: nucleic acid
        (C) STRANDEDNESS: double
        (D) TOPOLOGY: linear (xi) SEQUENCE DESCRIPTION: SEQ ID NO: 10:

```
CTA  TTA  CTG  CAG  GTA  TTC  TTC  CGG  GAT  TTC  TTC  GAA  GTC  GCC  GTC  GTT         48
     Gln  Leu  Tyr  Glu  Glu  Pro  Ile  Glu  Glu  Phe  Asp  Gly  Asp  Asn
     1                   5                        10

GTG  AGA  CTG  CGG  TTT  CGG  GGT  ACC  TTC  GCC  AGT  AAC  GCA  CTG  GTT  TTT         96
His  Ser  Gln  Pro  Lys  Pro  Thr  Gly  Glu  Gly  Thr  Val  Cys  Gln  Asn  Lys
15                       20                      25                      30

TTC  GCC  GTC  AGA  GCC  CAG  GAT  GCA  TTT  GTT  GCC  CTG  GCC  GCA  AAC  GTT        144
Glu  Gly  Asp  Ser  Gly  Leu  Ile  Cys  Lys  Asn  Gly  Gln  Gly  Cys  Val  Asn
               35                      40                      45

AGA  GCC  TTC  GCA  CAG  GCA  CAG  GTT  CTG  ACC  GGA  TTC  AGT  GCA  GTC  AGT        192
Ser  Gly  Glu  Cys  Lue  Cys  Leu  Asn  Gln  Gly  Ser  Glu  Thr  Cys  Asp  Thr
               50                      55                      60

GTA  AAC  AAC  CAT  GGT  TTT  GAT  ACG  CGG  TTT  GGT  TTT  TGA  ATT  CCC  CGG        240
Tyr  Val  Val  Met  Thr  Lys  Ile  Arg  Pro  Lys  Thr  Lys  Ser  Asn  Gly  Pro
          65                      70                      75

ATC  GTC  TTT  AAG  GCT  TTG  GAT  GAA  GCC  GTT  ACG  TTG  TTC  TTC  AGT  TAA        288
Asp  Asp  Lys  Leu  Ser  Gln  Ile  Phe  Gly  Asn  Arg  Gln  Glu  Glu  Thr  Leu
     80                      85                      90

GTT  AGG  TAA  AGT  TAA  AAT  TTC  ATA  GAA  AGC  ATT  TTG  TTG  TTC  TTT  GTT        336
Asn  Pro  Leu  His  Leu  Ile  Glu  Tyr  Phe  Ala  Asn  Gln  Gln  Glu  Lys  Asn
100                      105                     110                     120

GAA  TTT  GTT  GTC  AGC  TTT  TGG  TGC  TTG  AGC  ATC  ATT  TAG  CTT  TTT  AGC        384
Phe  Lys  Asn  Asp  Ala  Lys  Pro  Ala  Gln  Ala  Asp  Asn  Leu  Lys  Lys  Ala
               125                     130                     135

TTC  TGC  TAA  AAG  GTT  AGC  GCT  TTG  GCT  TGG  GTC  ATC  TTT  TAG  GCT  TTG        432
Glu  Ala  Leu  Leu  Asn  Ala  Ser  Gln  Ser  Pro  Asp  Asp  Lys  Leu  Ser  Gln
               140                     145                     150

GAT  GAA  ACC  ATT  GCG  TTG  TTC  TTC  GTT  TAA  GTT  AGG  TAA  ATG  TAA  GAT        480
Ile  Phe  Gly  Asn  Arg  Gln  Glu  Glu  Asn  Leu  Asn  Pro  Leu  His  Leu  Ile
          155                     160                     165

TTC  ATA  GAA  AGC  ATT  TTG  TTG  TTC  TTT  GTT  GAA  TTT  GTT  ATC  CGC  TTT        528
Glu  Tyr  Phe  Ala  Asn  Gln  Gln  Glu  Lys  Asn  Phe  Lys  Asn  Asp  Ala  Lys
     170                     175                     180

CGG  TGC  TTG  AGA  TTC  ATT  TAA  CTT  TTT  AGC  TTC  TGA  CAA  TAG  GTT  AGC        576
Pro  Ala  Gln  Ser  Glu  Asn  Leu  Lys  Lys  Ala  Glu  Ser  Leu  Leu  Asn  Ala
185                      190                     200                     205

ACT  TTG  GCT  TGG  GTC  ATC  TTT  TAA  GCT  CTG  GAT  GAA  ACC  ATT  GCG  TTG        624
Ser  Glu  Ser  Pro  Asp  Asp  Lys  Leu  Ser  Gln  Ile  Phe  Gly  Asn  Arg  Gln
               210                     215                     220

TTC  TTC  GTT  TAA  GTT  AGG  TAA  ATG  CAA  GAT  TTC  ATA  GAA  AGC  ATT  TTG        672
Glu  Glu  Asn  Leu  Asn  Pro  Leu  His  Leu  Ile  Glu  Tyr  Phe  Ala  Asn  Gln
          230                     235                     240
```

| | | | | | | | | | | | | | | | |
|---|---|---|---|---|---|---|---|---|---|---|---|---|---|---|---|
| TTG | TTC | TTT | GTT | GAA | ATT | GTT | AGA | AGC | TTC | TTT | CAG | GGT | TAT | GCG | TTG | 720 |
| Gln | Glu | Lys | Asn | Phe | Asn | Asn | Ser | Ala | Glu | Lys | Leu | Thr | Ile | Arg | Gln | |
| | | 245 | | | | | 250 | | | | | 255 | | | | |

| | |
|---|---|
| TTC | CAT | 726 |
| Glu | Met | |
| | 260 | |

HIRUDIN FUSION PROTEINS AND PREPARATION OF HIRUDIN

This application is a continuation of application Ser. No. 07/861,820, filed as PCT/EP90/02084, Dec. 4, 1990 published as WO91/09946, Jul. 11, 1991 now abandoned.

The present invention relates to a process for the preparation of hirudin with the aid of a novel fusion protein.

Hirudin has been known for a long time (cf. Merck Index 1983, No. 4613) and has anticoagulant properties. The structure of hirudin is likewise known (FEBS Lett. 165 (1984) 180). Hirudin may be sulfated on the amino acid tyrosine in position 63.

There have been attempts to prepare hirudin by gene manipulation (FEBS Lett. 202 (1986) 373, Biol. Chem. Hoppe-Seyler 367 (1986) 731). However, the yields were poor because hirudin was evidently unstable to proteolysis in the cell or expression was very low. Although expression as a fusion protein produced higher crude yields, in this case purification is very elaborate (DNA 5 (1986) 511).

We have now found that hirudin peptides can be prepared with good yields and straight forward purification via a fusion protein of the formula X—Z-hirudin peptide where X is protein A or one of its active polypeptide fragments, and Z is Met or an oligopeptide sequence which can be cleaved at the point of attachment to the hirudin or in the neighborhood thereof.

The term hirudin peptide includes hirudin, hirudin extended or truncated at the N terminus by 1–3 amino acids, and hirudin peptides with hirudin activity.

Protein A is a known protein (cf. EP 135 532). The term "active polypeptide fragment" of protein A means those protein A fragments which still have the ability to bind to immunoglobulin (cf. Biochemistry 20 (1981) 2361–96 and Eur. J. Biochem. 156 (1986) 637–43).

Z is Met or an oligopeptide sequence which is present neither in X nor in hirudin and which can be cleaved enzymatically or chemically at the point of attachment to the hirudin or in the neighborhood thereof. In the simplest case, Z is methionine.

The fusion protein can be cleaved by conventional methods. If Z is methionene, the cleavage can be carried out with cyanogen bromide, in which case X-homoserine and hirudin are liberated. When Y contains the sequence Asp-Pro, it is possible to use acids to cleave between these amino acids. In this case, the Asp residue remains on the protein A carboxyl terminus, and Pro remains on the hirudin N terminus. Other oligopeptide sequences suitable for Y are the following, inter alia: Asp↓Gly (cleavage by hydroxylamine), Pro-Phe-His-Leu↓Leu (enzymatic cleavage by renin), Ile-Glu-Gly-Arg↓hirudin (enzymatic cleavage by factor VIII).

Thus, depending on the oligopeptide Z used, either there is liberation of hirudin or hirudin peptide or the result is extended hirudin or hirudin peptides.

The hirudin peptide can have the originally published amino acid sequence (see FEBS Lett. 165 (1987 [sic]) 180) or the sequence of one of the isohirudins which have been found since (FEBS Lett. 255 (1989) 105–110) or of artificially prepared mutants with hirudin activity.

The present invention also relates to the abovementioned X—Z-hirudin fusion protein and the use thereof for the preparation of hirudin.

The fusion protein which was produced by replacing the 388 bp N-terminal protein A fragment from the commercial vector PRIT 2T [sic] (Pharmacia, Order No. 27-4808-01, FIG. 1) by a 97 bp synthetic adaptor (sequence 1) has proven particularly advantageous. The DNA sequence and the relevant amino acid sequence are depicted as sequence 7. Amino acids 1–8 stem from the N-terminus of the lambda phage cro gene. Amino acids 9–11 are a synthetic sequence. Amino acids 12–41 of SEQ ID NO. 9 correspond to amino acids 120–149 of the Uhlen et. al. protein A sequence (J. Biol. Chem. 259, 1697 (1984)), with the exception that Asn-Met in position 135–136 (Uhlen) has been replaced by His-Leu (amino acids 27–28 in SEQ ID NO. 9) in order to eliminate a Met. Amino acids 42–163 of SEQ ID NO. 9 correspond to amino acids 150–271 of the Uhlen et al. protein A sequence. Amino acids 176–240 are the hirudin sequence.

The fusion proteins have the following exceptional properties:

1) Very high-level expression is possible in *E. coli*.
2) They are very stable to proteolysis.
3) They are produced in soluble form in *E. coli*.
4) They are very stable to heat (up to ≦80° C.).
5) They bind to IgG-Sepharose exclusively via their protein A portion.

The fusion protein of Example 1 additionally has the following advantages:

a) Cleavage with BrCN produces mature hirudin without an additional N-terminal amino acid.
b) Since the methionine in the cleavage peptide [sic] is the only one in the fusion protein, cleavage produces two fragments. Of these, the fusion partner can be separated from hirudin by IgG affinity chromatography.

EXAMPLE 1

Figure 1:
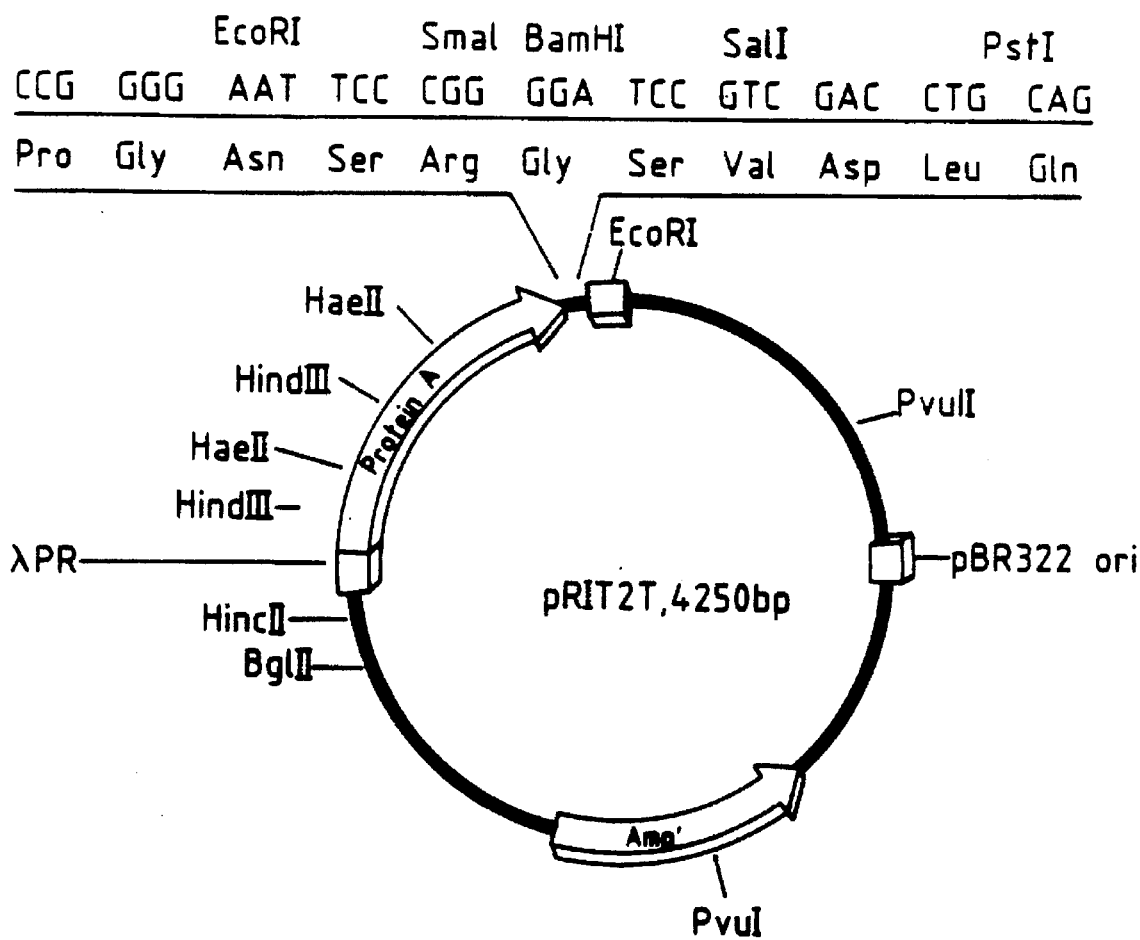
FIG. 1 depicts protein A expression vector pRIT 2T.

Preparation of the Expression Plasmid a) Construction of the vector:

The protein A vector pRIT 2T (FIG. 1) is commercially available and has been described in detail (Pharmacia Order No. 27-4808-01).

This vector was modified as follows: it was cleaved with the restriction endonuclease Hind III. The larger fragment (vector) was isolated from an agarose gel by electroelution. The complementary oligonucleotides Koe 1/2 (sequence 1) were ligated into this vector. The resulting chimeric plasmid was transformed into the lambda lysogenic strain N 4830-1 (Pharmacia Order No. 27-4808-01 [sic]). The clone with the correct orientation of the oligonucleotides was found, with the aid of Hind III/EcoRI restriction mapping, from among the possible recombinants, and was checked by DNA sequencing. This expression plasmid was called pRIT 2TA.

b) Insertion of a synthetic hirudin gene with adaptor

The pRIT 2TA DNA was cut with EcoRI and SalI, and the larger DNA fragment (a) was isolated from an agarose gel by electroelution.

A synthetic hirudin gene (sequence 6) was prepared using a DNA synthesizer (Applied Biosystems, model 380A). 4 Oligonucleotides (Koe 3-Koe 6; sequences 2–5) were prepared for this. The oligonucleotides were kinased and ligated to the EcoRI/SalI-linearized plasmid pUC 18. The construct was checked by DNA sequencing. The hirudin gene (b) including the adaptor was cut out of this chimeric plasmid (pUC 18-Hir) with EcoRI and isolated by agarose gel electrophoresis and electroelution. Besides two stop codons at the 3' end and the SalI recognition site, the synthetic hirudin gene contains an adaptor sequence which links the hirudin gene to the protein A fusion partner via the EcoRI cleavage site, with retention of the reading frame.

Figure 2:
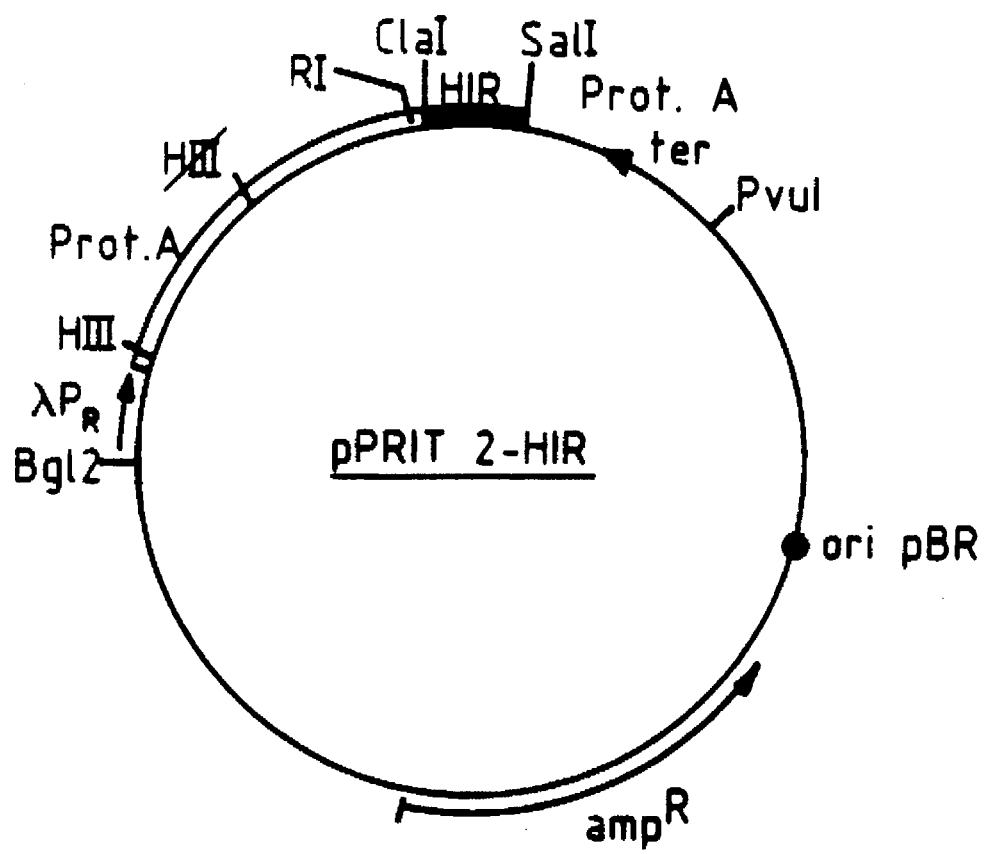
FIG. 2 depicts protein A-hirudin expression vector pRIT2TA-Hir.

The isolated DNA fragments a and b were ligated together and transformed into the lysogenic strain N 4830 -1. This resulted in the protein A-hirudin expression vector pRIT2TA-Hir (FIG. 2).

EXAMPLE 2

Expression of the Fusion Protein

The expression plasmid pRIT 2TA-Hir was transformed into the *E. coli* strain N 4830-1 (Pharmacia Order No. 27-4808-01 [sic]). This strain contains the thermosensitive lambda repressor CI [sic] 857 in the chromosome.

100 ml of MIM medium (MIM=32 g of tryptone, 20 g of yeast extract, 6 g of $Na_2HPO_4$, 3 g of $KH_2PO_4$, 0.5 g of NaCl, 1 g of $NH_4Cl$ per liter and 0.1 mM $MgSO_4$ plus 0.001 mM $FeCl_3$) were sterilized in a 1 l Erlenmeyer flask with baffles, and ampicillin was added (ad 100 µg/ml). The medium was inoculated with 1 ml of a fresh overnight culture of the strain pRIT 2TA-Hir/N 4830-1 and incubated at 28° C. with shaking, until the absorption at 550 nm was 0.6. Then 100 ml of fresh MIM/amp medium at 65° C. were added, and incubation was continued at 42° C. for 4 h. The desired fusion protein was synthesized during this time. The cell walls were removed enzymatically by adding lysozyme to 75 mg/l and incubation (37° C., 3 h). It was then possible to disrupt these cells mechanically (Manton-Gaulin press, freezing cycle, vigorous stirring), by a heat shock up to 80° C. or by hypotonic lysis, to release the soluble fusion protein into the medium.

EXAMPLE 3

Purification of the Fusion Protein

The cell fragments were removed by centrifugation, and the clear supernatant was pumped through an IgG-Sepharose column (IgG Sepharose® 6 Fast Flow, Pharmacia, Order No. 17-0969-01). The manufacturer's instructions were followed in the storage of the column material, preparation and setting up of the column, application conditions and flow :rates. Thus, a 200 ml gel bed and a flow rate of about 3 l/h were used for 6 l of supernatant. In this step the fusion protein was reversibly bound via its IgG-binding protein A portion to the gel matrix (yield about 95%). After application, the column was washed with 10 bed volumes of TST (50 mM tris-HCl, pH 7.6; 150 mM NaCl and 0.05% Tween®20) and eluted with 0.5M acetate buffer, pH 2.8.

EXAMPLE 4

Cleavage of the Fusion Protein

The column eluate from Example 3 was lyophilized and stored at −20° C. For the cleavage, it was taken up in 70% strength formic acid to a protein concentration of about 25 g/l. After flushing with argon, 1 g of solid BrCN was added per g of fusion protein to cleave off the hirudin. The cleavage took place under argon at 37° C. in about 4 h. The excess cyanogen bromide, the solvent and other volatile components were removed by lyophilization. The material was then washed three times with water.

EXAMPLE 5

Renaturation and Purification of the hirudin

The lyophilizate was taken up in 6M guanidinium hydrochloride, 0.1M tris/HCl, pH 8.5, 0.2M DTT to a protein concentration of 1–100 mg/ml. The sample was incubated for 2 h and then desalted by G-10 exclusion chromatography (equilibrated with 10M HCl). The desalted sample was diluted 1:20 in 0.1M tris/HCl, 5 mM GSH/0.5 mM GSSG, 1 mM EDTA, pH 8.7 and incubated for 1 h (GSH is reduced and GSSH [sic] is oxidized glutathione). This treatment increased the specific activity of the hirudin by a factor of 3–5. The pH was adjusted to 7.6 with HCl, NaCl was added to 150 mM and Tween®20 was added to 0.05%, and then the IgG-Sepharose chromatography was repeated (Example 3). While the protein A fusion partner and uncleaved fusion protein were bound to the column, the active hirudin was present with a purity >90% in the flow-through. Classical methods of protein chemistry could be used to purify it to clinical purity.

Sequences

Sequence 1:

|  | Hind III |  | Ser | Asn | Asn | Phe | Asn | Lys | Glu | Gln | Gln | Asn | Ala | Phe |
|---|---|---|---|---|---|---|---|---|---|---|---|---|---|---|
| Koe 1: Seq ID NO: 1 | 5'-A | GCT | TCT | AAC | AAT | TTC | AAC | AAA | GAA | CAA | CAA | AAT | GCT | TTC |
| Koe 2: Seq ID NO: 2 |  | 3'- | AGA | TTG | TTA | AAG | TTG | TTT | CTT | GTT | GTT | TTA | CGA | AAG |

| Tyr | Glu | Ile | Leu | His | Leu | Pro | Asn | Leu | Asn | Glu | Glu | Gln | Arg | Asn | Gly |
|---|---|---|---|---|---|---|---|---|---|---|---|---|---|---|---|
| TAT | GAA | ATC | TTG | CAT | TTA | CCT | AAC | TTA | AAC | GAA | GAA | CAA | CGC | AAT | GGT |
| ATA | CTT | TAG | AAC | GTA | AAT | GGA | TTG | AAT | TTG | CTT | CTT | GTT | GCG | TTA | CCA |

|  |  | Hind III |  |  |
|---|---|---|---|---|
| Phe | Ile | Gln |  |  |
| TTC | ATC | CAG-3' |  |  |
| AAG | TAG | GTC | TCG | A-5' |

Sequence 2
Koe 3: Seq ID NO: 3     5'- AATTCAAAAA CCAAACCGCG TATCAAAACC ATGGTTGTTT ACACTGACTG CACTGAATCC
                           GGTCAGAACC TGTGCCTGTG CGAAGGCTCT AACGTTTGCG GCCAGGGCAA CAAATGCATC
                           CTGGGCTCT-3'

Sequence 3
Koe 4: Seq ID NO: 4     5'- GACGGCGAAA AAAACCAGTG CGTTACTGGC GAAGGTACCC CGAAACCGCA GTCTCACAAC

| Sequences | | |
|---|---|---|
| | | GACGGCGACT TCGAAGAAAT CCCGGAAGAA TACCTGCAGT AATAGG-3' |
| Sequence 4 | | |
| Koe 5: Seq ID NO: 5 | | 5'- TCGACCTATT ACTGCAGGTA TTCTTCCGGG ATTTCTTCGA AGTCGCCGTC GTTGTGAGAC TGCGGTTTCG GGGTACCTTC GCCAGTAACG CACTGGTTTT TTTCGCCGTC AGAGCCCAGG ATGCATTT-3' |
| Sequence 5 | | |
| Koe 6: Seq ID NO: 6 | | 5'- GTTGCCCTGG CCGCAAACGT TAGAGCCTTC GCACAGGCAC AGGTTCTGAC CGGATTCAGT GCAGTCAGTG TAAACAACCA TGGTTTGATA CGCGGTTTGG TTTTTG-3' |
| Sequence 6 | | |
| Koe 7: Seq ID NO: 7 | | 5'- AATTCAAAAA CCAAACCGCG TATCAAAACC ATGGTTGTTT ACACTGACTG CACTGAATCC |
| Eco RI Seq ID NO: 8 | | 3'-GTTTTT GGTTTGGCGC ATAGTTTTGG TACCAACAAA TGTGACTGAC GTGACTTAGG |
| | | GGTCAGAACC TGTGCCTGTG CGAAGGCTCT AACGTTTGCG GCCAGGGCAA CAAATGCATC CCAGTCTTGG ACACGGACAC GCTTCCGAGA TTGCAAACGC CGGTCCCGTT GTTTACGTAG |
| | | CTGGGCTCTG ACGGCGAAAA AAACCAGTGC GTTACTGGCG AAGGTACCCC GAAACCGCAG GACCCGAGAC TGCCGCTTTT TTTGGTCACG CAATGACCGC TTCCATGGGG CTTTGGCGTC |
| | | TCTCACAACG ACGGCGACTT CGAAGAAATC CCGGAAGAAT ACCTGCAGTA ATAGG-3'  SalI AGAGTGTTGC TGCCGCTGAA GCTTCTTTAG GGCCTTCTTA TGGACGTCAT TATCCAGCT-5' |

Sequence 7

| | | | | | 5 | | | | | 10 | | | | | 15 | | |
|---|---|---|---|---|---|---|---|---|---|---|---|---|---|---|---|---|---|
| | Met | Glu | Gln | Arg | Ile | Thr | Leu | Lys | Glu | Ala | Ser | Asn | Asn | Phe | Asn | Lys | |
| Seq ID NO: 9 | ATG | GAA | CAA | CGC | ATA | ACC | CTG | AAA | GAA | GCT | TCT | AAC | AAT | TTC | AAC | AAA | 48 |
| Seq ID NO: 10 | TAC | CTT | GTT | GCG | TAT | TGG | GAC | TTT | CTT | CGA | AGA | TTG | TTA | AAG | TTG | TTT | 48 |

| | | 20 | | | | | 25 | | | | | 30 | | | |
|---|---|---|---|---|---|---|---|---|---|---|---|---|---|---|---|
| Glu | Gln | Gln | Asn | Ala | Phe | Tyr | Glu | Ile | Leu | His | Leu | Pro | Asn | Leu | Asn |
| GAA | CAA | CAA | AAT | GCT | TTC | TAT | GAA | ATC | TTG | CAT | TTA | CCT | AAC | TTA | AAC | 96 |
| CTT | GTT | GTT | TTA | CGA | AAG | ATA | CTT | TAG | AAC | GTA | AAT | GGA | TTG | AAT | TTG | 96 |

| | | 35 | | | | | 40 | | | | | 45 | | | |
|---|---|---|---|---|---|---|---|---|---|---|---|---|---|---|---|
| Glu | Glu | Gln | Arg | Asn | Gly | Phe | Ile | Gln | Ser | Leu | Lys | Asp | Asp | Pro | Ser |
| GAA | GAA | CAA | CGC | AAT | GGT | TTC | ATC | CAG | AGC | TTA | AAA | GAT | GAC | CCA | AGC | 144 |
| CTT | CTT | GTT | GCG | TTA | CCA | AAG | TAG | GTC | TCG | AAT | TTT | CTA | CTG | GGT | TCG | 144 |

| | 50 | | | | | 55 | | | | | 60 | | | | |
|---|---|---|---|---|---|---|---|---|---|---|---|---|---|---|---|
| Glu | Ser | Ala | Asn | Leu | Leu | Ser | Glu | Ala | Lys | Lys | Leu | Asn | Glu | Ser | Gln |
| CAA | AGT | GCT | AAC | CTA | TTG | TCA | GAA | GCT | AAA | AAG | TTA | AAT | GAA | TCT | CAA | 192 |
| GTT | TCA | CGA | TTG | GAT | AAC | AGT | CTT | CGA | TTT | TTC | AAT | TTA | CTT | AGA | GTT | 192 |

| 65 | | | | | 70 | | | | | 75 | | | | | 80 |
|---|---|---|---|---|---|---|---|---|---|---|---|---|---|---|---|
| Ala | Pro | Lys | Ala | Asp | Asn | Lys | Phe | Asn | Lys | Glu | Gln | Gln | Asn | Ala | Phe |
| GCA | CCG | AAA | GCG | GAT | AAC | AAA | TTC | AAC | AAA | GAA | CAA | CAA | AAT | GCT | TTC | 240 |
| CGT | GGC | TTT | CGC | CTA | TTG | TTT | AAG | TTG | TTT | CTT | GTT | GTT | TTA | CGA | AAG | 240 |

| | | | | 85 | | | | | 90 | | | | | 95 | |
|---|---|---|---|---|---|---|---|---|---|---|---|---|---|---|---|
| Tyr | Glu | Ile | Leu | His | Leu | Pro | Asn | Leu | Asn | Glu | Glu | Gln | Arg | Asn | Gly |
| TAT | GAA | ATC | TTA | CAT | TTA | CCT | AAC | TTA | AAC | GAA | GAA | CAA | CGC | AAT | GGT | 288 |
| ATA | CTT | TAG | AAT | GTA | AAT | GGA | TTG | AAT | TTG | CTT | CTT | GTT | GCG | TTA | CCA | 288 |

| | | | | 100 | | | | | 105 | | | | | 110 | |
|---|---|---|---|---|---|---|---|---|---|---|---|---|---|---|---|
| Phe | Ile | Gln | Ser | Leu | Lys | Asp | Asp | Pro | Ser | Gln | Ser | Ala | Asn | Leu | Leu |
| TTC | ATC | CAA | AGC | CTA | AAA | GAT | GAC | CCA | AGC | CAA | AGC | GCT | AAC | CTT | TTA | 336 |
| AAG | TAG | GTT | TCG | GAT | TTT | CTA | CTG | GGT | TCG | GTT | TCG | CGA | TTG | GAA | AAT | 336 |

| | | 115 | | | | | 120 | | | | | 125 | | | |
|---|---|---|---|---|---|---|---|---|---|---|---|---|---|---|---|
| Ala | Glu | Ala | Lys | Lys | Leu | Asn | Asp | Ala | Gln | Ala | Pro | Lys | Ala | Asp | Asn |
| GCA | GAA | GCT | AAA | AAG | CTA | AAT | GAT | GCT | CAA | GCA | CCA | AAA | GCT | GAC | AAC | 384 |
| CGT | CTT | CGA | TTT | TTC | GAT | TTA | CTA | CGA | GTT | CGT | GGT | TTT | CGA | CTG | TTG | 384 |

| | | 130 | | | | | 135 | | | | | 140 | | | |
|---|---|---|---|---|---|---|---|---|---|---|---|---|---|---|---|
| Lys | Phe | Asn | Lys | Glu | Gln | Gln | Asn | Ala | Phe | Tyr | Glu | Ile | Leu | His | Leu |
| AAA | TTC | AAC | AAA | GAA | CAA | CAA | AAT | GCT | TTC | TAT | GAA | ATT | TTA | CAT | TTA | 432 |
| TTT | AAG | TTG | TTT | CTT | GTT | GTT | TTA | CGA | AAG | ATA | CTT | TAA | AAT | GTA | AAT | 432 |

| 145 | | | | | 150 | | | | | 155 | | | | | 160 |
|---|---|---|---|---|---|---|---|---|---|---|---|---|---|---|---|
| Pro | Asn | Leu | Thr | Glu | Glu | Gln | Arg | Asn | Gly | Phe | Ile | Gln | Ser | Leu | Lys |
| CCT | AAC | TTA | ACT | GAA | GAA | CAA | CGT | AAC | GGC | TTC | ATC | CAA | AGC | CTT | AAA | 480 |
| GGA | TTG | AAT | TGA | CTT | CTT | GTT | GCA | TTG | CCG | AAG | TAG | GTT | TCG | GAA | TTT | 480 |

| | | | | 165 | | | | | 170 | | | | | 175 | |
|---|---|---|---|---|---|---|---|---|---|---|---|---|---|---|---|
| Asp | Asp | Pro | Gly | Asn | Ser | Lys | Thr | Lys | Pro | Arg | Ile | Lys | Thr | Met | Val |

Sequences (continued)

|  |  |  |  |  |  |  |  |  |  |  |  |  |  |  |  |  |
|---|---|---|---|---|---|---|---|---|---|---|---|---|---|---|---|---|
|  | GAC | GAT | CCG | GGG | AAT | TCA | AAA | ACC | AAA | CCG | CGT | ATC | AAA | ACC | ATG | GTT | 528 |
|  | CTG | CTA | GGC | CCC | TTA | AGT | TTT | TGG | TTT | GGC | GCA | TAG | TTT | TGG | TAC | CAA | 528 |
|  |  |  | 180 |  |  |  |  | 185 |  |  |  | 190 |  |  |
| Val | Tyr | Thr | Asp | Cys | Thr | Glu | Ser | Gly | Gln | Asn | Leu | Cys | Leu | Cys | Glu |
| GTT | TAC | ACT | GAC | TGC | ACT | GAA | TCC | GGT | CAG | AAC | CTG | TGC | CTG | TGG | GAA | 576 |
| CAA | ATG | TGA | CTG | ACG | TGA | CTT | AGG | CCA | GTC | TTG | GAC | ACG | GAC | ACG | CTT | 576 |
|  | 185 |  |  |  |  | 190 |  |  |  | 195 |  |  |  |
| Gly | Ser | Asn | Val | Cys | Gly | Gln | Gly | Asn | Lys | Cys | Ile | Leu | Gly | Ser | Asp |
| GGC | TCT | AAC | GTT | TGC | GGC | CAG | GGC | AAC | AAA | TGC | ATC | CTG | GGC | TCT | GAC | 624 |
| CCG | AGA | TTG | CAA | ACG | CCG | GTC | CCG | TTG | TTT | ACG | TAG | GAC | CCG | AGA | CTG | 624 |
|  | 200 |  |  |  | 205 |  |  |  |  | 210 |  |  |  |
| Gly | Glu | Lys | Asn | Gln | Cys | Val | Thr | Gly | Glu | Gly | Thr | Pro | Lyi | Pro | Gln |
| GGC | GAA | AAA | AAC | CAG | TGC | GTT | ACT | GGC | GAA | GGT | ACC | CCG | AAA | CCG | CAG | 672 |
| CCG | CTT | TTT | TTG | GTC | ACG | CAA | TGA | CCG | CTT | CCA | TGG | GGC | TTT | GGC | GTC | 672 |
| 215 |  |  |  |  | 220 |  |  |  |  | 225 |  |  |  | 230 |
| Ser | His | Asn | Asp | Gly | Asp | Phe | Glu | Glu | Ile | Pro | Glu | Glu | Tyr | Leu | Gln |
| TCT | CAC | AAC | GAC | GGC | GAC | TTC | GAA | GAA | ATC | CCG | GAA | GAA | TAC | CTG | CAG | 720 |
| AGA | GTG | TTG | CTG | CCG | CTG | AAG | GTT | CTT | TAG | GGC | CTT | CTT | ATG | GAC | GTC | 720 |
| Stop | Stop |
| TAA | TAG | 726 |
| ATT | ATC | 726 |

---

We claim:

1. A fusion protein of the formula I $$X-Z-\text{hirudin peptide} \qquad I$$

where X is an amino acid sequence comprising an active fragment of protein A, Z is Met or an oligopeptide sequence which can be cleaved at the point of attachment to the hirudin peptide between X and the hirudin peptide, said fusion protein being expressed from a pRIT 2TA expression vector.

2. A fusion protein comprising an active fragment of protein A linked to hirudin with Met as depicted in SEQ ID No. 9.

3. A method for the preparation of hirudin, comprising expressing a fusion protein comprising an active fragment of protein A linked to hirudin with Met from *E. coli* transfected with pRIT 2TA, isolating the fusion protein, and cleaving the fusion protein with CNBr to obtain hirudin.

4. The method of claim 3, wherein the fusion protein expressed is depicted in SEQ ID No. 9.

* * * * *